United States Patent
Tatsumi et al.

(10) Patent No.: US 6,509,487 B2
(45) Date of Patent: Jan. 21, 2003

(54) PROCESS FOR PRODUCING LOWER ALKYL FATTY ESTERS

(75) Inventors: Nobuhiro Tatsumi, Wakayama (JP); Takanobu Katayama, Wakayama (JP); Osamu Tabata, Wakayama (JP); Taku Mimura, Wakayama (JP); Noriaki Fukuoka, Wakayama (JP); Katsutoshi Yamamoto, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/989,409

(22) Filed: Nov. 21, 2001

(65) Prior Publication Data

US 2002/0062035 A1 May 23, 2002

(30) Foreign Application Priority Data

Nov. 22, 2000 (JP) ........................ 2000-355377

(51) Int. Cl.$^7$ .................................. C11C 3/00
(52) U.S. Cl. ...................... 554/167; 554/162
(58) Field of Search .................. 554/162, 167

(56) References Cited

U.S. PATENT DOCUMENTS 5,008,046 A    4/1991   Bremus et al.

FOREIGN PATENT DOCUMENTS

| JP | 53-6161 | 3/1978 |
| JP | 53 006161 B | 3/1978 |
| JP | 1-283251 | 11/1989 |
| JP | 07 224002 A | 8/1995 |
| JP | 7-224002 | 8/1995 |

*Primary Examiner*—Deborah D. Carr
(74) *Attorney, Agent, or Firm*—Birch, Stewart, Kolasch & Birch, LLP

(57) ABSTRACT

The present invention provides a process for producing lower alkyl fatty esters from fatty acids and lower alcohols, wherein lower alkyl fatty esters are produced in higher yield with a reduction in the amount of the remaining fatty acids. The process of the present invention comprises bringing fatty acids into contact with gaseous lower alcohols in fixed bed(s) charged with a weakly acidic solid catalyst by countercurrent operation, by co-current operation and subsequent countercurrent operation or by pseudo-countercurrent operation, thus feeding and reacting the fatty acids and lower alcohols in fixed-bed reactor(s) charged with a weakly acidic solid catalyst to produce lower alkyl fatty esters.

7 Claims, 7 Drawing Sheets

PROCESS FOR PRODUCING LOWER ALKYL FATTY ESTERS

TECHNICAL FIELD

The present invention relates to a process for producing lower alkyl fatty esters from fatty acids in fixed-bed reactor (s) charged with a weakly acidic solid catalyst by countercurrent or pseudo-countercurrent operation.

PRIOR ART

The lower alkyl fatty esters have been produced from of old as the starting material for producing higher alcohols, and methyl fatty esters are generally obtained by reaction of triglycerides with methanol or by reaction of fatty acids with methanol. In the reaction of triglycerides with methanol, glycerin is formed as a byproduct, but the formed methyl fatty esters and glycerin are easily separated as different phases, and thus the reaction easily proceeds. On the other hand, the reaction of fatty acids with methanol is an equilibrated reaction so that unless water formed as a byproduct is efficiently removed, the apparent rate of the reaction is lowered or the equilibrium of the reaction is established at a higher concentration of remaining fatty acids, and thus the amount of the remaining fatty acids cannot be sufficiently lowered.

To solve these problems, JP-A 1-283251 discloses a method of using a multi-stage-plate reaction column and reducing the pressure in the top of the reaction column. In this method, removal of water is improved by reduced pressure, but the catalyst used in esterification is a uniform catalyst, so removal of the catalyst from the desired products i.e. methyl fatty esters is necessary.

On the other hand, JP-B 53-6161 discloses a process for producing lower alkyl fatty esters by means of a fixed bed. It is described that in this process, a mixed solution of fatty acid and alcohol is brought into contact with a catalyst layer and the alcohol is gasified, but in this process, the operation of only co-current of fatty acid and alcohol is conducted, and water formed as a byproduct is evaporated into the gas phase but partially remains from the relationship of gas-liquid equilibrium. As the reaction proceeds, the content of water in the gas phase particularly in the vicinity of an outlet of the reaction column is increased so that from the relationship of gas-liquid equilibrium, the content of water in the liquid phase is also increased, thus making it difficult to lower the amount of the remaining fatty acid because of the equilibrated reaction. For lowering the content of water in the liquid phase, a method of using a large amount of alcohol can be anticipated but is not economical.

JP-A 7-224002(JP-B2 2707063) discloses a fixed-bed system for esterification wherein a strong acid catalyst and ion-exchange resin are used as the catalyst.

DISCLOSURE OF THE INVENTION

The object of the present invention is to provide a process for producing lower alkyl fatty esters from fatty acids and lower alcohols, wherein lower alkyl fatty esters are produced in higher yield with a reduction in the amount of the remaining fatty acids.

The invention provides a process for producing a lower alkyl fatty ester, which comprises feeding a fatty acid and a lower alcohol in a fixed-bed reactor charged with a weakly acidic solid catalyst and reacting them with each other by bringing the fatty acid into contact with gas of the lower alcohol in countercurrent operation in the bed.

The invention also provides a process for producing a lower alkyl fatty ester, which comprises feeding a fatty acid and a lower alcohol in at least two fixed-bed reactors charged with a weakly acidic solid catalyst and reacting them with each other by bringing the fatty acid into contact with gas of the lower alcohol in co-current operation in one of the reactors and then in countercurrent operation in the other reactor. It is here preferable that the gaseous lower alcohol is first fed to the countercurrent fixed-bed reactor and then gaseous lower alcohol discharged from the outlet of the reactor is fed to the co-current fixed-bed reactor.

The invention then provides a process for producing a lower alkyl fatty ester, which comprises feeding a fatty acid and a lower alcohol in multi-staged fixed-bed reactors each charged with a weakly acidic solid catalyst and reacting them with each other by feeding the fatty acid to a reactor at an upstream stage and sending it to a stage at the downstream side, feeding the gaseous lower alcohol to a reactor at a downstream stage to carry out downward co-current operation and at the same time returning the gaseous lower alcohol discharged from the outlet of the reactor to a stage at the upstream side to repeatedly conducting a pseudo-countercurrent operation in the fixed bed of each reactor.

DETAILED DESCRIPTION OF THE INVENTION

The fatty acids used in this invention include, but are not limited to, saturated or unsaturated fatty acids obtained by hydrolysis of natural vegetable and animal fats and oils. The vegetable fats and oils include e.g. coconut oil, palm oil, palm kernel oil, soybean oil etc. The animal fats and oils include e.g. tallow, lard, fishoil etc. Further, organic acids such as dicarboxylic acids and tricarboxylic acids can be mentioned. These are used preferably in a liquid form.

The lower alcohols used in the present invention are preferably $C_{1-5}$ lower alcohols. Specifically, monoalkanols such as methanol, ethanol and propanol can be mentioned, and methanol is industrially preferable because of low cost and easy recovery.

It is preferable the weakly acidic solid catalyst has a strong acid point of not higher than 0.2 mmol/g-Cat and a weak acid point of not less than 0.3 mol/g-Cat, each acid point being defined as follows:

Weak acid point: the point at which desorption of $NH_3$ occurs in the range of 100 to 250° C. in TPD (ammonia adsorption-desorption process);

Strong acid point: the point at which desorption of $NH_3$ occurs at a temperature higher than 250° C. in TPD.

It is further preferable that the weakly acidic solid catalyst is a molded article of a weakly acidic solid catalyst having the structure (A), the structure (B) and the metal atom (C) as follows:

Structure (A): a structure of an inorganic phosphoric acid wherein the hydrogen atom is removed from at least one OH group thereof, Structure (B): a structure of an organic phosphoric acid represented by the formula (1) or (2), wherein the hydrogen atom is removed from at least one OH group thereof:

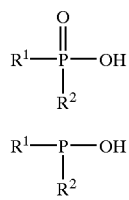

(1)

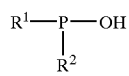

(2)

wherein —$R^1$ and —$R^2$ is independently selected from the group consisting of —R, —OR, —OH and —H and at least one of —$R^1$ and —$R^2$ is —R or —OR, —R being a $C_{1-22}$ organic group, and Metal atom (C): at least one metal atom selected from the group consisting of aluminum, gallium, and iron.

It is much preferable that the weakly acidic solid catalyst is a molded article of a heterogeneous catalyst comprising aluminum orthophosphate.

In the structure (A), the inorganic phosphoric acid includes orthophosphoric acid, metaphosphoric acid and condensed phosphoric acid such as pyrophosphoric acid, and in respect of performance, orthophosphoric acid is preferable. In the structure (B), the organic phosphoric acid represented by formula (1) or (2) includes phosphonic acid, monophosphonate, phosphinic acid, monophosphate, diphosphate, monophosphite and diphosphite or a mixture thereof, preferably phosphonic acid.

The organic group —R in the organic phosphoric acid is preferably an alkyl group such as methyl, ethyl, n-propyl, iso-propyl, n-butyl, iso-butyl, tert-butyl, n-hexyl, 2-ethylhexyl, octyl, dodecyl and octadecyl, and an aryl group such as phenyl and 3-methylphenyl, to which an amino group, alkoxy group, carbonyl group, alkoxycarbonyl group, carboxylic acid group, halogen group such as chloro group, phosphonic acid group, sulfonic acid group may be added.

In respect of performance and/or cost, the metal atom (C) is preferably aluminum. For the purpose of improving performance such as selectivity etc., the catalyst may contain a small amount of metal atoms other than aluminum, gallium and iron. It is not always necessary that all metal atoms (C) contained in the catalyst are bonded to the structure (A) or (B), and therefore, a part of metal atoms (C) may be present in the form of metal oxide, metal hydroxide etc.

Another preferable example of the weakly acidic solid catalyst of the present invention is a molded, heterogeneous catalyst containing aluminum orthophosphate, preferably having a pore diameter of 6 to 100 nm, a pore capacity of at least 0.46 ml/g, and an acid content of at least 0.40 mmol/g.

The process for producing the weakly acidic solid catalyst in the present invention includes a precipitation method, a method of impregnating a metal oxide or hydroxide with an inorganic phosphoric acid and an organic phosphoric acid, and a method of replacing an inorganic phosphoric acid group of an inorganic aluminum phosphate gel in part by an organic phosphoric acid group. The precipitation method is preferably used.

In preparing the catalyst of the present invention, a carrier having a large surface area may coexist to give the catalyst carried thereon. As the carrier, silica, alumina, silica alumina, titania, zirconia, diatomaceous earth, charcoal etc. can be used. When the carrier is used in excess, the content of the active component is lowered and in consequence the activity is lowered, and therefore the proportion of the carrier in the catalyst is preferably not higher than 90% by weight.

For molding the catalyst of the present invention, a molding additive is also preferably used. As the molding additive, zirconium or titanium hydroxide can be used.

It is preferable that an hydroxide of zirconium or titanium is used as the molding additive, optionally having the formula: MO(2−x/2) (OH)x, M standing for Zr or Ti, X standing for a number of 1 to 4, including at least one hydroxy group. A hydrate of the hydroxide may be also used. Typical examples thereof include zirconium hydroxide, titanium hydroxide, zirconium oxyhydrate, titanium oxyhydroxide and hydrates thereof. Zirconium hydroxide is more preferable from the viewpoint of mechanical strength of the mold.

The molding additive is commercially available. Alternatively it can be produced in a usual manner. For example, a water-soluble compound of zirconium or titanium, such as oxychloride, chloride, nitrate, oxynitrate and sulfate, maybe neutralized with an alkali. An alkoxide of zirconium or titanium may be hydrolyzed.

The weakly acidic solid catalyst of the invention can be produced by mixing powder of a metal salt of a phosphorus-containing acid with a molding additive to obtain a mold article of the metal salt of the phosphorus-containing acid. It is preferable from the viewpoint of improvement in molding and performance of powder to use 2 to 80 wt. %, more preferably 5–50 wt. %, much more preferably 10–50 wt. % of a molding addtive to the dry powder of a metal salt of a phosphorus-containing acid. The amount of the molding additive is determined in term of oxide of zirconium or titanium contained in the hydroxide.

Further a binder of an organic or inorganic compound may be added. Another additive of an organic or inorganic compound or a fine pore-forming agent maybe added to improve plasticity, lubrication and wetting.

The binder may include an inorganic compound such as alminasol, titaniasol, zirconiasol, silicasol and sol of an oxide complex thereof and an organic compound of a cellulose derivative such as methylcellulose and carboxymethylcellulose.

The other additive may include sugars, crystalline celluloses, starches, a polyhydric alcohol such as ethylene glycol, glycerin, sorbitol, polyethylene glycol and polyvinylalcohol, graphite, activated carbon, an organic polymer such as polyethylene, methyl polymethacrylate and nylon, soap such as magnesium stearate and sodium stearate and a surfactant such as an aliphatic alcohol, an aliphatic acid, an aliphatic acid ester, an aliphatic acid amide and polyoxyethylenealkylether.

The mixing can be effected by a usual mixer, for example together with water or an organic solvent such as ethanol, methanol, acetone and 2-propanol. The temperature and the time is not specified.

The obtained mixed powder product may be molded by a usual molder such as an extruder, a roller molder and a presser. The powder can be improved in fluidity when flowing in the molding machine is an important factor, for example in an extruder or a roller molder. The molded article is not specified in shape.

Composition of the Molded Catalyst

The molded catalyst produced in the method of the present invention is used usually via a drying step (degreasing step and calcination step). The composition (excluding molding additives if any other than zirconium or titanium hydroxide) of the molded product after drying at a temperature of 200° C. or more comprises 20 to 98%, preferably 50 to 95% and more preferably 50 to 90% by weight of a phosphorus-containing acid metal salt. The composition (excluding molding additives if any other than zirconium or titanium hydroxide) of the molded product further comprises 1.2 to 65% by weight of at least one metal selected from zirconium and titanium. In particular when zirconium hydroxide is used as a molding additive, the molded catalyst comprises zirconium in an amount of preferably 1.5 to 59.2% by weight, more preferably 3.7 to 37% by weight and most preferably 7.4 to 37% by weight. When titanium hydroxide is used as a molding additive, the molded catalyst comprises titanium in an amount of preferably 1.2 to 48% by weight, more preferably 3 to 30% by weight and most preferably 6 to 30% by weight.

Further, the composition of the molded product after drying at a temperature of 200° C. or more comprises preferably 1 to 80%, more preferably 2 to 50% and most preferably 2 to 30% by weight of molding additives such as binder other than zirconium or titanium hydroxide.

Heretofore, solid acid catalysts have been used in esterification reaction in a fixed bed, and the solid acid catalysts used are those having carriers such as porous materials carrying, or impregnated with, an acid such as sulfuric acid, p-toluenesulfonic acid (PTS), chlorosulfonic acid or methylsulfonic acid, or cation-exchange resin, H-form zeolite, H-form montmorilonite etc. However, these solid acid catalysts are so strongly acidic catalysts that side reactions such as formation of ether derivatives by dehydro-condensation of lower alcohols proceeds. Further, if the reaction temperature is raised-to improve the reactivity, unfavorable side reactions occur further significantly.

The weakly acidic solid catalyst used in the present invention is mainly a catalyst having a weak acid point so that even if the reaction temperature is raised, the progress of side reactions is extremely low, and therefore the reaction temperature can be set high, the temperature of the main reaction can also be raised, and thus the volume of the reactor can be reduced.

BRIEF DESCRIPTION OF THE DRAWINGS

In the fixed-bed reaction system in the present invention, lower alcohols are gasified and reacted in the 3 phases of gas-liquid-solid. The direction of gas-liquid flow in the present invention is most preferably a gas-liquid countercurrent. FIG. 1 shows an outline of a reactor where the countercurrent operation is conducted. The important feature for the countercurrent operation lies in selection of conditions not to cause flooding (phenomenon where the downward flow of liquid is prevented by the upward flow of gas). For preventing flooding in case the grain size of the catalyst is too small, the flow rate of fatty acid liquid and lower alcohol gas cannot be raised as desired, and therefore productivity may not be improved in some cases. Further, when lower alkyl fatty esters are produced industrially in a large-scale fixed-bed reactor, the sectional area of the fixed-bed reactor is increased less in many cases than the amount of the catalyst charged, resulting in an increase in the flow rate of liquid and gas to cause flooding easily.

In this case, it is preferable to use a method wherein two operations in two or more fixed-bed reactors are conducted in combination, for example the co-current operation is conducted in one fixed-bed reactor and then the countercurrent operation is conducted in another reactor (e.g. FIG. 2). By this operation, the reaction can proceed until the chemical equilibrium between gas and liquid is reached in the first co-current operation. In the subsequent countercurrent operation, it is sufficient to merely supply an alcohol gas to react with the remaining unreacted fatty acids, and thus a smaller amount of alcohol gas fed can be set. Accordingly, flooding may be prevented in the countercurrent operation to reduce the flow rate of the alcohol gas. That is, as shown in FIG. 2, an alcohol gas is fed initially to a solid fixed-bed reactor where the countercurrent operation is conducted, and then the excess alcohol gas discharged from the outlet of the reactor is subjected as it is or together with an additional alcohol gas to the co-current operation in another solid fixed-bed reactor, which may be followed by the countercurrent operation.

Another preferable embodiment of the present invention involves pseudo-countercurrent operation (assuming the feature of countercurrent operation in the entire facilities), which is actually co-current operation in the individual fixed-bed reactors but can be regarded as countercurrent operation in view of the entire facilities. That is, the preferable embodiment of the present invention is a process for producing lower alkyl fatty esters which comprises conducting pseudo-countercurrent operation in multi-stage solid fixed-bed reactors each charged with a weakly acidic solid catalyst wherein co-current operation is repeatedly carried out by feeding fatty acids to a reactor at an upper stage, preferably at the uppermost stage and then to a stage at the downstream side preferably one after another while feeding gaseous lower alcohols to a reactor at a lower stage, preferably at the lowermost stage and returning gaseous lower alcohols discharged from-the outlet of the reactor to a stage at the upstream side preferably one after another. As used herein, "a stage at the upstream side" refers to a stage nearer to the fixed-bed reactor to which starting fatty acids are first fed, while "the uppermost stage" refers to a stage at the uppermost side.

Figure 3:
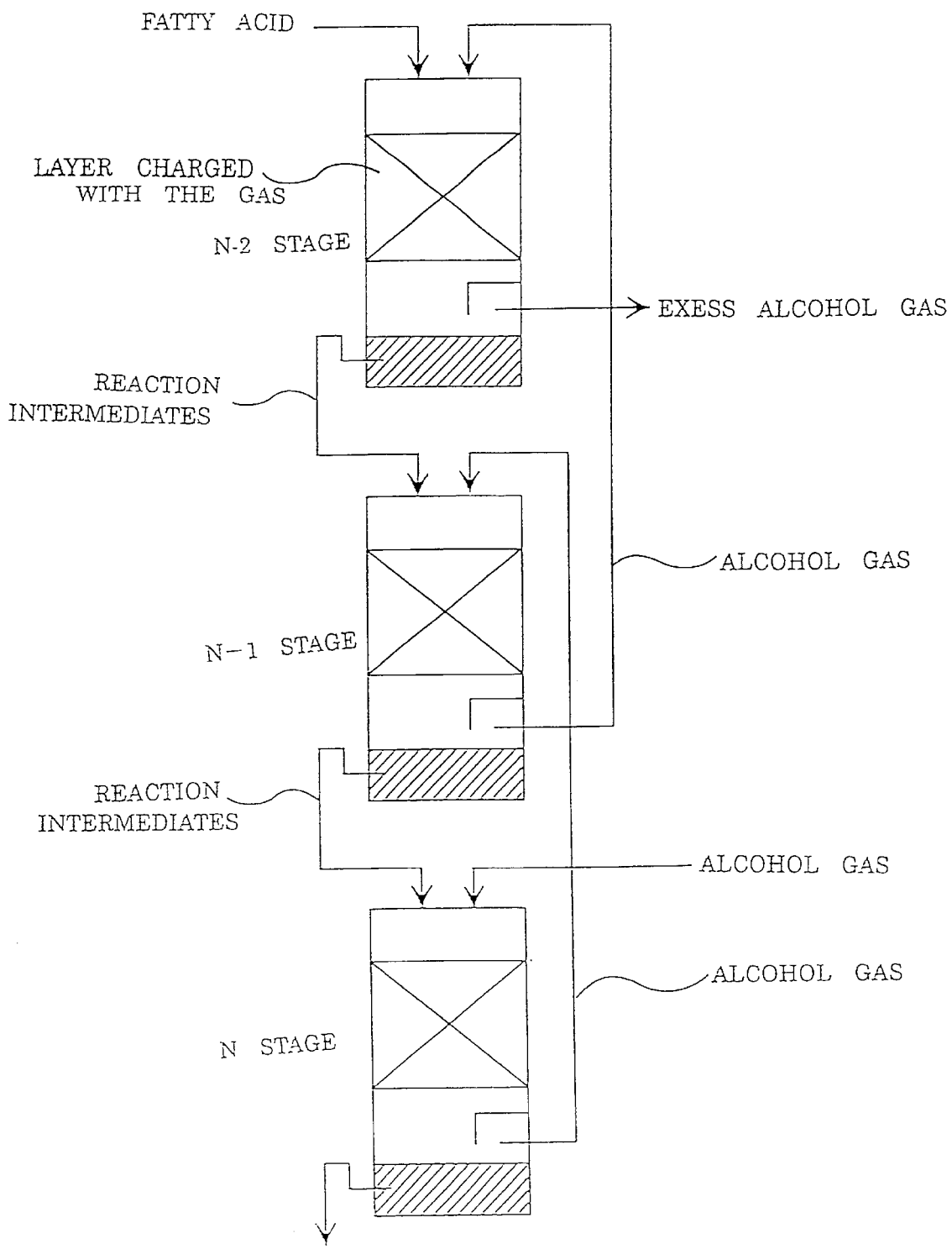
FIG. 3 shows an outline of a reactor and the flow of gas and liquid where pseudo-countercurrent operation is conducted in trickle flow in the present invention.
Figure 4:
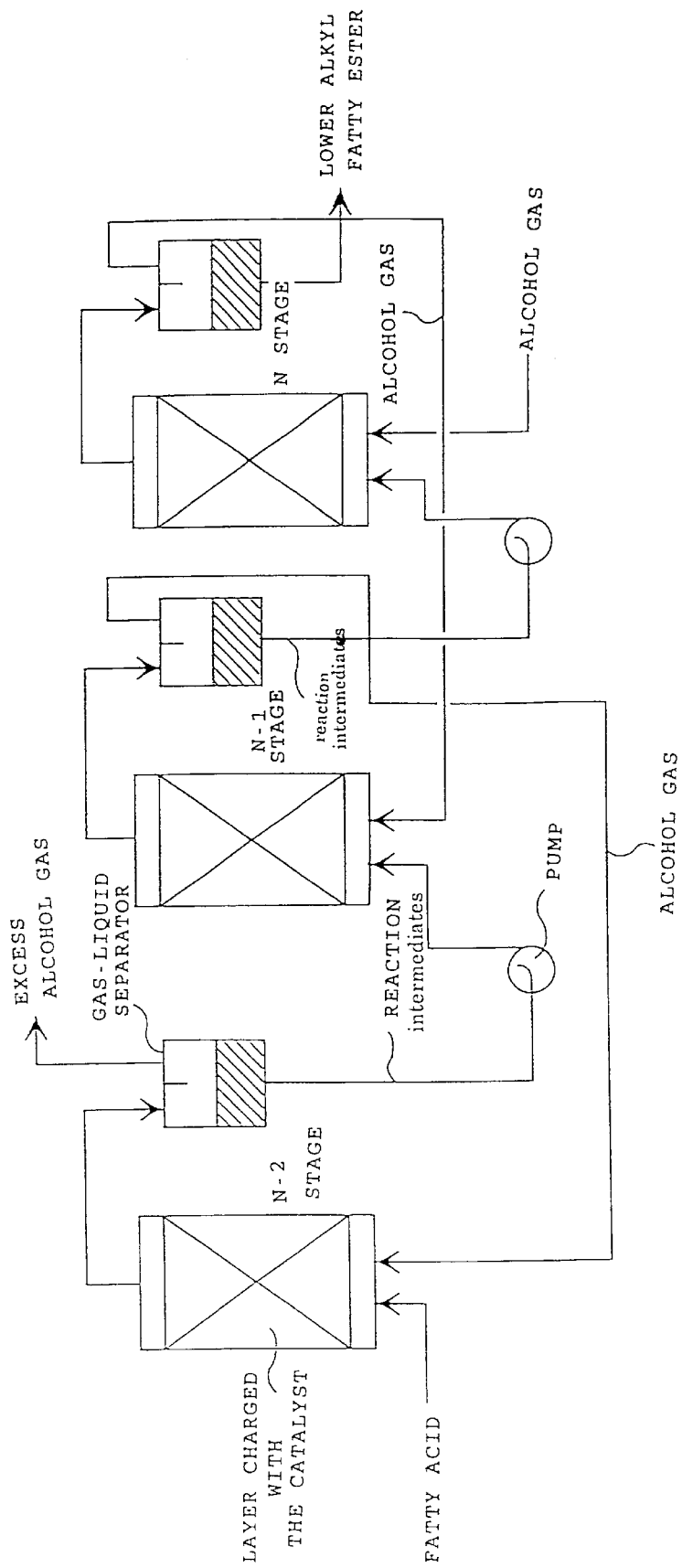
FIG. 4 shows an outline of a reactor and the flow of gas and liquid where the pseudo-countercurrent operation is conducted in up-flow in the present invention.

In this case, the direction of the flow of gas and liquid in each fixed-bed reactor may be a co-current downward flow (trickle flow) as shown in FIG. 3 or a co-current upward flow (up-flow) as shown in FIG. 4. In the case of the trickle flow, a plurality of fixed-bed reactors each charged with a weakly acidic solid catalyst are arranged at multi-stages in series, and fatty acids are fed to a reactor at an upper stage, preferably at the uppermost stage and then to lower stages preferably one after another, while gaseous lower alcohols are fed to the top of a reactor at a lower stage, preferably at the lowermost stage and contacted in co-current downward flow with the liquid (fatty acids) from an upper stage, and then gaseous lower alcohols after gas-liquid separation are fed to the top of a reactor at an upper stage and contacted with fatty acids in co-current downward flow in the same manner as above. This operation is conducted repeatedly whereby the fatty acids are sent from the upper to lower stages while the lower alcohol gas is sent from the lower to upper stages so that in view of the entire facilities, it seems as if countercurrent operation was conducted (pseudo-countercurrent operation) although co-current operation is actually conducted in individual reactors. In this embodiment, therefore, the yield of the desired products i.e. lower alkyl fatty esters can be increased while the amount of the remaining fatty acids can be reduced.

In this embodiment, there does not occur the phenomenon of flooding where the downward flow of liquid is prevented by the upward flow of gas, and thus the flow rate of fluid and gas can be set arbitrarily.

In the case of the up-flow, on the other hand, a liquid feed pump and a gas-liquid separator are arranged among a plurality of fixed-bed reactors at respective stages. The liquid is fed to the bottom of an upstream stage, preferably of the uppermost stage, while a gas-liquid phase flow overflowed form the column is separated into gas and liquid, and the liquid is fed by a pump to the bottom of the next downstream stage. On the other hand, the gas is fed to the bottom of a lower stage, preferably of the lowermost stage, and after separation, is fed to the bottom of a stage at the downstream side. This operation is conducted repeatedly so that in view of the whole system, it seems as if countercurrent operation was conducted although co-current operation is actually conducted at each stage. Similarly to the case of the above-described trickle flow, the yield of lower alkyl fatty esters can be increased, the amount of the remaining fatty acids can be reduced, and the phenomenon of flooding can be prevented, thus enabling arbitrary setting of flow rates of fluid and gas.

Figure 2:
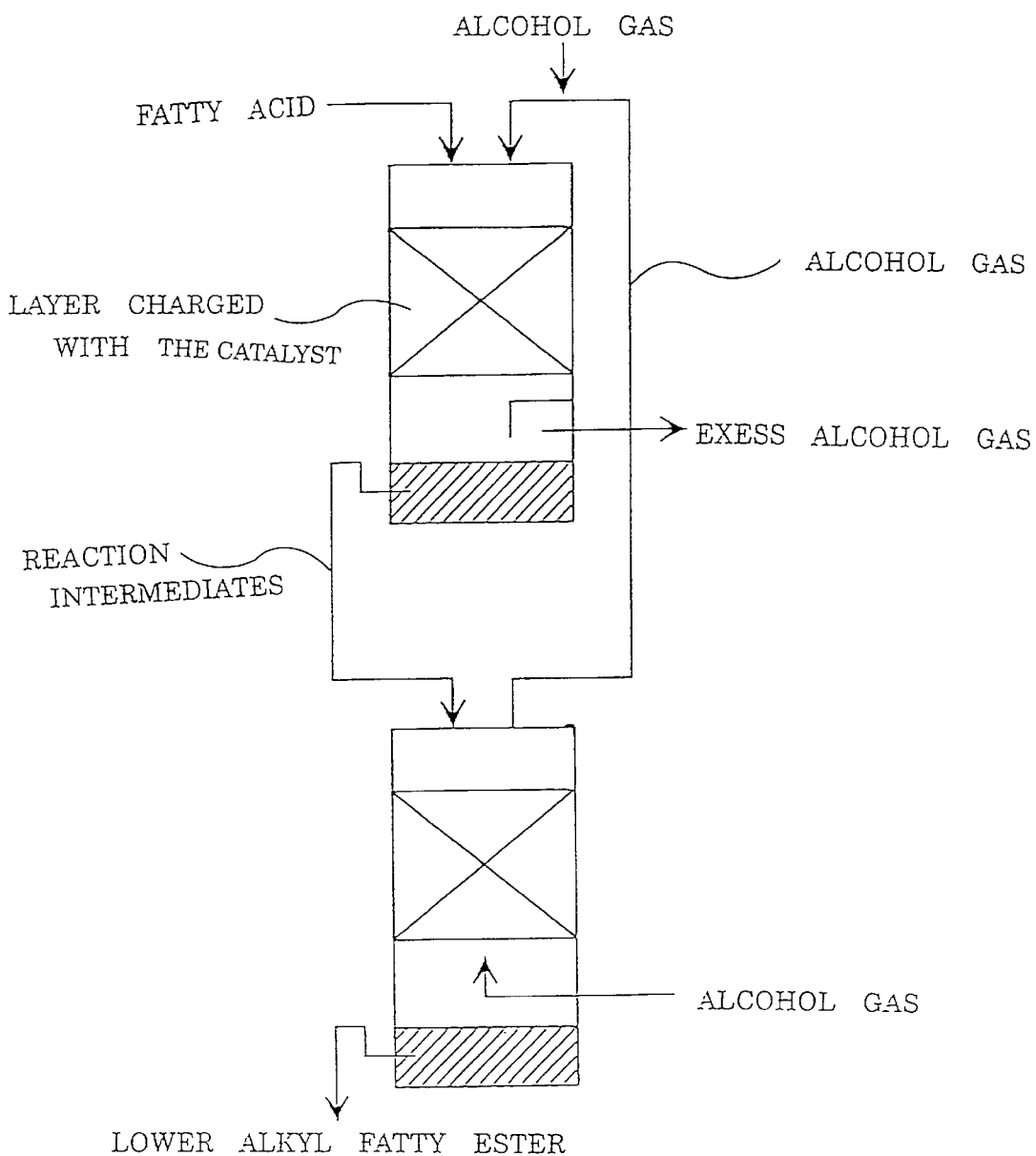
FIG. 2 shows an outline of a reactor and the flow of gas and liquid where co-current and countercurrent operations are conducted in this order in the present invention.

As the number of stages in fixed-bed reactors is increased, the operation brings about better results similar to those of co-current operation, but usually 2 to 5 stages are preferable for operativeness and from an economical point of view. FIGS. 2 and 3 show facilities consisting of a plurality of independent fixed-bed reactors, which however may be formed into one reaction tower provided with a plurality of independent fixed-bed reactors. The structure of the gas-liquid separator in this case is not particularly limited, and can be of bubble-cap type or in the form shown in FIGS. 2 and 3. For the type shown in FIG. 4, the gas-liquid separation may be carried out with a gas-liquid separation vessel, separately provided as shown in the drawing.

Figure 5:
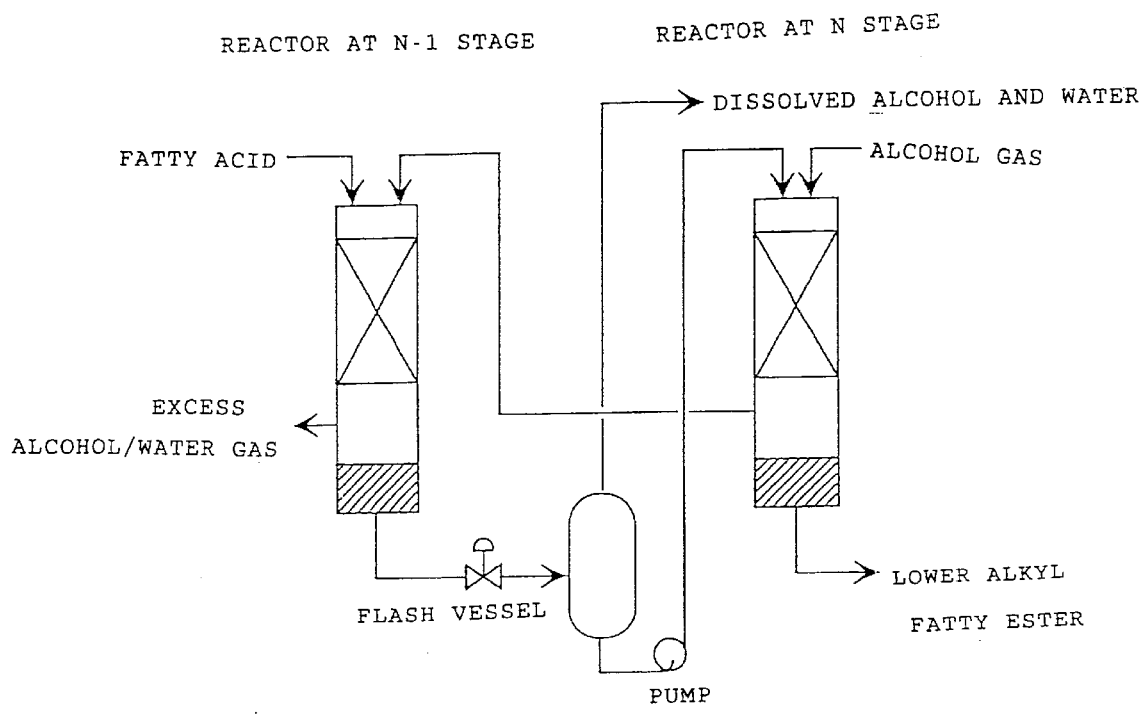
FIG. 5 shows an outline of a reactor and the flow of gas and liquid where pseudo-countercurrent operation is conducted in trickle flow while removing water in the liquid in the present invention.

As shown in FIG. 5, the liquid separated in the gas-liquid separator in the reactor at the previous stage may be flashed to remove water therein.

By doing so, entrained water in the reactor at the downstream side is reduced so that the reaction equilibrium is shifted toward a direction for achieving higher reactivity.

Figure 6:
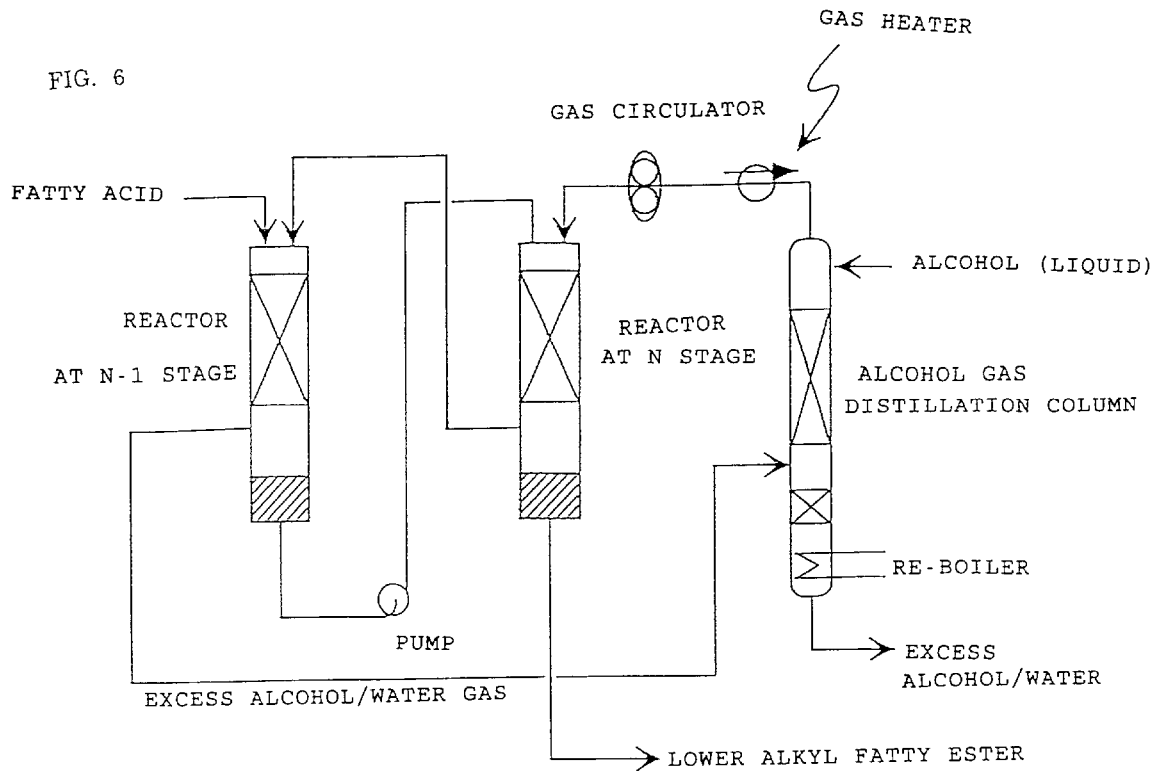
FIG. 6 show s an outline of a reactor and the flow of gas and liquid where pseudo-countercurrent operation is conducted in trickle flow while reusing the gas after reaction by circulation in the present invention.

Further, the gas after the reaction may be reused by circulation as shown in FIG. 6. For reuse, the alcohols should be refined in a distillation column or through a membrane. If the alcohol gas is reused by circulation, the molar ratio of the actually used alcohols can be reduced and simultaneously the heating for gasification of the gas can be reduced economically.

The starting low alcohols are recovered and reusable without condensation.

From the viewpoint of improving productivity per unit volume of the reactor and of achieving sufficient reactivity, the liquid hourly space velocity (LHSV) of the fatty acids fed to the fixed-bed reactor is usually preferably 0.1 to 10/Hr, more preferably 0.2 to 5/Hr.

From the viewpoint of reducing the amount of remaining fatty acids and the amount of alcohols recovered, the molar ratio of lower alcohols to fatty acids is usually preferably 1 to 100, more preferably 2 to 10. These lower alcohols are gasified in a usual manner e.g. by heating evaporation etc.

The superficial velocity of the alcohol gas in the column in the countercurrent operation is suitably established depending on the grain size of the weakly acidic solid catalyst and the liquid hourly space velocity (LHSV) of fatty acids fed, but from the viewpoint of improving productivity and preventing flooding, the superficial velocity of the alcohol gas in the column in the co-currrent operation, is preferably 0.01 to 3 m/sec., more preferably 0.01 to 2 m/sec. More specifically, when the grain size of the weakly acidic solid catalyst is 0.5 mm, the superficial velocity is preferably 0.01 to 1.0 m/sec., more preferably 0.01 to 0.8 m/sec. and most preferably 0.02 to 0.3 m/sec.

In the co-current operation, flooding does not occur, and thus the superficial velocity of the gas in the column is not particularly limited, but from the viewpoint of improving productivity, lowering pressure loss due to gas flow and reducing the amount of alcohols recovered, the superficial velocity of the gas is preferably 0.01 to 50 m/sec., more preferably 0.01 to 30 m/sec. As used herein, the superficial velocity of the gas in the column refers to the velocity of the gas at the operation temperature and at the operation pressure.

For the viewpoint of sufficiently activating the catalyst to effect the reaction economically and of lessening a condensate of two alcohol molecules to reduce the loss in alcohols, the reaction temperature is usually preferably 50 to 250° C., more preferably 60 to 220° C.

The reaction pressure is not particularly limited, but the reaction under pressure is preferable because the concentration of lower alcohols in the liquid phase is increased owing to the gas-liquid equilibrium relationship, thus improving the reaction rate particularly at an initial stage of the reaction. The reaction pressure is preferably 7 MPa or less, more preferably 4 MPa or less and most preferably 2 MPa or less, at which lower alcohols are not liquefied and the gas-liquid countercurrent or pseudo-countercurrent operation is facilitated. If the reaction is allowed to proceed at a lower reaction temperature to minimize byproducts formed, the reaction is preferably conducted under reduced pressure for lowering the boiling point of lower alcohols. In this case, the pressure is preferably −0.08 MPa or more, more preferably −0.05 MPa or more, at which the solubility of lower alcohol liquid phase is not lowered, fatty acids and fatty esters is prevented from being gasified, and the gas-liquid countercurrent or pseudo-countercurrent operation is facilitated.

The reaction products obtained in the manner described above contain an excess of dissolved lower alcohols in addition to the desired lower alkyl fatty esters. By removing these lower alcohols in a usual manner e.g. by topping from the reaction products discharged from the outlet of the fixed-bed reactor, the desired lower alkyl fatty esters can be isolated.

According to the present process for producing lower alkyl fatty esters from fatty acids and lower alcohols, remaining fatty acids can be reduced to a very low concentration and simultaneously the corresponding lower alkyl fatty esters can be produced in higher yield by countercurrent or pseudo-countercurrent operation of fatty acids and gaseous lower alcohols in fixed beds charged with a weakly acidic solid catalyst. Further, if the catalyst is diluted and charged into a reactor, the cost of the catalyst can be reduced while the yield of the desired products is maintained.

EXAMPLES

Production Example 1

9.9 g ethylphosphonic acid, 27.7 g of 85% orthophosphoric acid and 112.5 g aluminum nitrate ($9H_2O$) were dissolved in 1000 g water. The pH value of this mixed solution was increased to 5 by dropwise adding ammonia water. During the reaction, gel-like white precipitates were formed. The precipitates were separated by filtration, washed with water, dried at 110° C. for 15 hours and ground into 60 mesh or less powder. 10% alumina sol was added to this ground catalyst, which was then extrusion-molded into a molded product of 1.5 mmφ. This product was calcined at 250° C. for 3 hours to give a molded, weakly acidic solid catalyst (referred to hereinafter as catalyst 1).

Production Example 2

147 g of 85% phosphoric acid (Katayama Kagaku Kogyo Co., Ltd.), 49.5 g ethylsulfonic acid (Nippon Chemical Industrial Co., Ltd.) and 563 g aluminum nitrate $9H_2O$ (Katayama Kagaku Kogyo Co., Ltd.) were dissolved in 5 L deionized water. 10% ammonia water was added dropwise thereto at 35° C. for about 3 hours to adjust the mixture to pH 5, whereby precipitates were obtained. The resulting precipitates were separated by filtration and repeatedly washed with water until the conductivity of the filtrate was lowered to 1 mS/cm. The cake washed with water was dried overnight at 110° C. and ground into 0.25 mm or less powder as phosphorus-containing acid metal salt powder.

17.5 g (ignition loss at 250° C. or less: 2.5 g) of this phosphorus-containing acid metal salt powder, 7.6 g zirconium hydroxide (zirconium hydroxide R whose zirconia content is 40%, manufactured by Daiichi Kigenso Kagaku Kogyo Co., Ltd.), 0.15 g methyl cellulose (Shin-Etsu Chemical Co., Ltd.) and 5.0 g titania sol (titania content of 30%, stabilized with nitric acid, manufactured by Ishihara Techno Co., Ltd.) were sufficiently mixed with a mixer, and 8.3 g water was added thereto and kneaded. The kneaded cake was extrusion-extruded through an opening of 1.7 mm in diameter by pressurization at a pressure of about 3 MPa and then calcined at 320° C. to give catalyst 2.

Example 1

Figure 1:
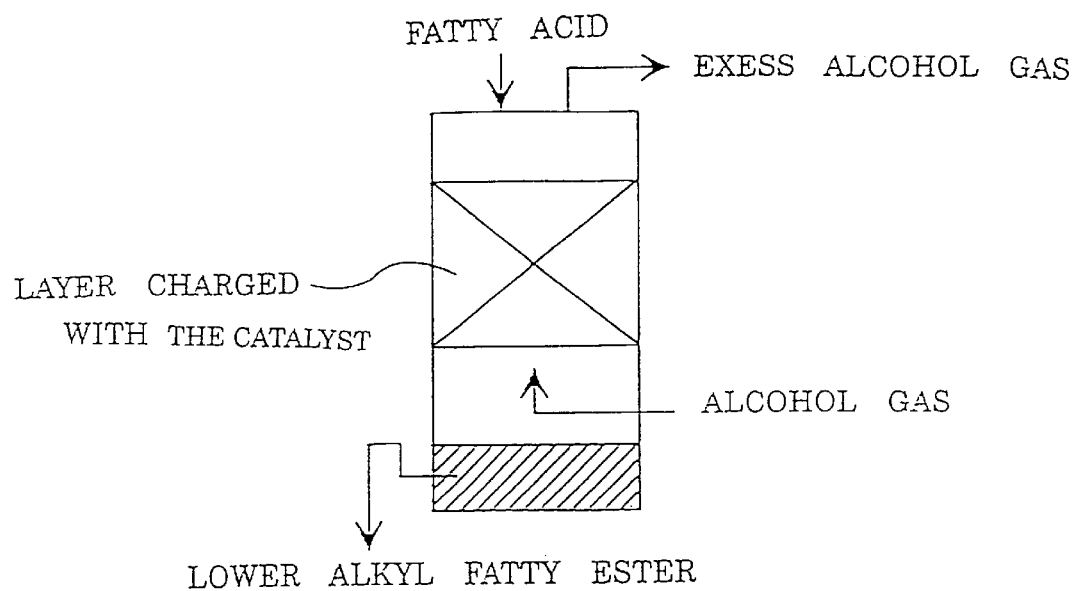
FIG. 1 shows an outline of a reactor and the flow of gas and liquid where countercurrent operation is conducted in the present invention.

200 cc catalyst 1 was charged into the bottom of a first reactor of 28 mmφ in inner diameter and 400 mmH in height having a gas-liquid separator. As shown in FIG. 1, a methanol gas was fed to the bottom of the reactor. As the fatty acid, a mixture of lauric acid/myristic acid in a ratio of 75 wt-%/25 wt-% (acid value=270.6) was fed to the top of the reactor, and the gas-liquid countercurrent reaction was conducted. The fatty acids were fed in a LHSV of 0.6 relative to the amount of the catalyst. Further, the amount of the methanol gas fed was in 5-fold molar excess relative to the amount of the fatty acids fed. The reaction pressure was 0.5 MPa-G, and the reaction temperature was 200° C.

The reaction product was sampled from the outlet of the reactor, and methanol/water was removed from the resulting reaction product by topping etc. As a result of determination of the remaining fatty acids and the lower alkyl fatty esters, the fatty acids were 0.34% by weight, and the methyl fatty esters were 99.66% by weight.

Example 2

300 cc catalyst 1 was charged into the bottom of a first reactor of 35.5 mmφ in inner diameter and 520 mmH in height having a gas-liquid separator. Similarly, 150 cc catalyst 1 was charged into the bottom of a second reactor of 35.5 mmφ in inner diameter and 520 mmH in height having a gas-liquid separator. These reactors were connected in series, and as shown in FIG. 3, a methanol gas was fed to the second reactor and then via the gas outlet of the second reactor to the first reactor. As the fatty acid, a mixture of lauric acid/myristic acid in a ratio of 75 wt-%/25 wt-% (acid value=270.6) was fed to the first reactor, and the liquid separated in the gas-liquid separator in the first reactor was fed to the second reactor. The fatty acids were fed such in a LHSV of 0.7 relative to the total amount of the catalysts in the 2 stages. Further, the amount of the methanol gas fed was in 5-fold molar excess relative to the amount of the fatty acids fed. The reaction pressure was 1.0 MPa-G, and the reaction temperature was 200° C.

The reaction product was sampled from the outlet of each reactor, and methanol/water was removed from the resulting reaction product by topping etc. As a result of determination of the remaining fatty acids and the lower alkyl fatty esters, the fatty acids were 8.12% by weight and the methyl fatty esters were 91.88% by weight in the outlet of the first reactor, while in the outlet of the second reactor, the fatty acids were 0.29% by weight and the methyl fatty esters were 99.71% by weight. The amount of dimethyl ether (DME) formed as a byproduct was 0.176% by weight relative to the amount of the starting material methanol.

Example 3

300 cc catalyst 1 was charged into the bottom of a first reactor of 35.5 mmφ in inner diameter and 520 mmH in height having a gas-liquid separator. Similarly, 75 cc catalyst 1 was charged into the bottom of a second reactor of 35.5 mmφ in inner diameter and 520 mmH in height having a gas-liquid separator. As shown in FIG. 3, a methanol gas was fed to the second reactor and then via the gas outlet of the second reactor to the first reactor in the same manner as in Example 2. As the fatty acid, a mixture of lauric acid/myristic acid in a ratio of 75 wt-%/25 wt-% (acid value=270.6) was fed to the first reactor, and the liquid separated in the gas-liquid separator in the first reactor was fed to the second reactor. The fatty acids were fed in a LHSV of 0.43 relative to the total amount of the catalysts in the 2 stages. Further, the amount of the methanol gas fed was in 5-fold molar excess relative to the amount of the fatty acids fed. The reaction pressure was 1.0 MPa-G, and the reaction temperature was 200° C.

The reaction product was sampled from the outlet of the reactor, and methanol/water was removed from the resulting reaction product by topping etc., and as a determination of the remaining fatty acids and the lower alkyl fatty esters, the fatty acids were 4.29% by weight and the methyl fatty esters were 95.71% by weight in the outlet of the first reactor, while in the outlet of the second reactor, the fatty acids were 0.17% by weight and the methyl fatty esters were 99.83% by weight. The amount of DME formed as a byproduct was 0.190% by weight relative to the amount of the starting material methanol.

Example 4

24 L catalyst 2 was charged into the bottom of a first reactor of 203 mmφ in inner diameter and 1450 mm in height having a gas-liquid separator. Further, 8 L catalyst 2 was charged into a second reactor of 130 mmφ in inner diameter and 1305 mm in height having a gas-liquid separator.

Figure 8:
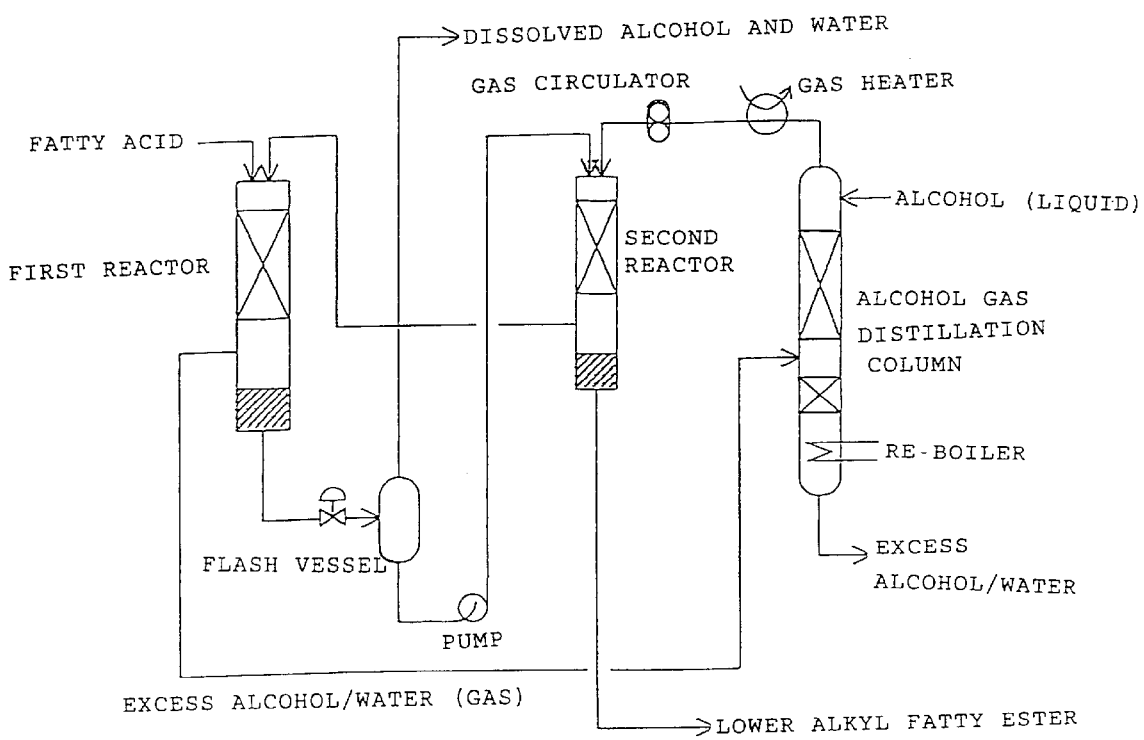
FIG. 8 shows an outline of a reactor used in Example 4 and the flow of gas and liquid.

As shown in FIG. 8, methanol (liquid) was fed as reflux fluid to an alcohol gas distillation column, and the gas recovered from the reaction system was refined in the alcohol gas distillation column, and the methanol gas was circulated and reused in the reaction. The amount of methanol (liquid) was 8.4 kg/h, and the methanol gas was circulated at a rate of 13 kg/h. As the fatty acid, a mixture of lauric acid/myristic acid in a ratio of 70 wt-%/30 wt-% was fed at a rate of 13 kg/h to the top of the first reactor and subjected to the gas-liquid co-current reaction with the recovered methanol supplied from the second reactor. After the reaction in the portion of the charged catalyst, the reaction products separated in the gas-liquid separator in the first reactor were fed via a flash vessel under reduced pressure to the top of the second reactor. Together with the refined methanol gas, the reaction products were introduced and reacted in the portion of the charged catalyst in the second reactor to give final products.

The reaction pressure was 0.75 MPa-G, and the reaction temperature was regulated in the range of 170 to 175° C. Methanol/water was removed from the resulting reaction products by topping etc. As a result of determination of the remaining fatty acids and the lower alkyl fatty esters, the fatty acids were 0.12% by weight, and the methyl fatty esters were 99.88% by weight.

Comparative Example 1

Figure 7:
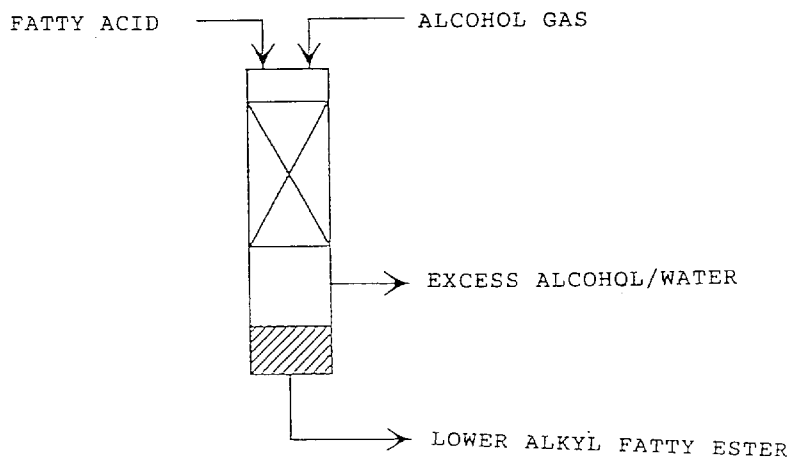
FIG. 7 shows an outline of a reactor used in Comparative Examples 1 and 2 and the flow of gas and liquid.

300 cc catalyst 1 was charged into the bottom of a first reactor of 35.5 mmφ in inner diameter and 520 mmH in height having a gas-liquid separator. As shown in FIG. 7, a methanol gas was fed to the top of the reactor. As the fatty acid, a mixture of lauric acid/myristic acid in a ratio of 75 wt-%/25 wt-% (acid value=270.6) was fed to the top of the reactor, and the gas-liquid co-current reaction was conducted. The fatty acids were fed in a LHSV of 0.5 relative to the amount of the catalyst. Further, the amount of the methanol gas fed was in 5-fold molar excess relative to the amount of the fatty acids fed. The reaction pressure was 1.0 MPa-G, and the reaction temperature was 200° C.

The reaction products were sampled from the outlet of the reactor, and methanol/water was removed from the resulting reaction products by topping etc. As a result of determination of the remaining fatty acids and the lower alkyl fatty esters, the fatty acids were 3.95% by weight, and the methyl fatty esters were 96.05% by weight. The amount of DME formed as a byproduct was 0.162% by weight relative to the amount of the starting material methanol.

Comparative Example 2

200 cc strongly acidic ion-exchange resin (Diaion RCP-160H manufactured by Mitsubishi Kagaku Co., Ltd.) as a catalyst previously swollen with methanol was charged into the bottom of a first reactor of 28 mmφ in inner diameter and 400 mmH in height having a gas-liquid separator. As shown in FIG. 7, a methanol gas was fed to the top of the reactor. As the fatty acid, lauric acid (acid value=280.9) was fed to the top of the reactor, and the gas-liquid co-current reaction was conducted. The fatty acid was fed in a LHSV of 0.5 relative to the amount of the catalyst. Further, the amount of the methanol gas fed was in 5-fold molar excess relative to the amount of the fatty acid fed. The reaction pressure was atmospheric pressure, and the reaction temperature was 110° C. The reaction products were sampled from the outlet of the reactor, and methanol/water was removed from the resulting reaction products by topping etc. As a result of determination of the remaining fatty acid and the lower alkyl fatty ester, the fatty acid was 2.71% by weight, and the methyl fatty ester was 97.29% by weight. The amount of DME formed as a byproduct was 0.532% by weight relative to the amount of the starting material methanol.

What is claimed is:

1. A process for producing a lower alkyl fatty ester, which comprises feeding a fatty acid and a lower alcohol in a fixed-bed reactor charged with a weakly acidic solid catalyst and reacting them with each other by bringing the fatty acid into contact with gas of the lower alcohol in countercurrent operation in the bed.

2. A process for producing a lower alkyl fatty ester, which comprises feeding a fatty acid and a lower alcohol in at least two fixed-bed reactors charged with a weakly acidic solid catalyst and reacting them with each other by bringing the fatty acid into contact with gas of the lower alcohol in co-current operation in one of the reactors and then in countercurrent operation in the other reactor.

3. The process according to claim 2, wherein the gaseous lower alcohol is first fed to the countercurrent fixed-bed reactor and then gaseous lower alcohol discharged from the outlet of the reactor is fed to the co-current fixed-bed reactor.

4. A process for producing a lower alkyl fatty ester, which comprises feeding a fatty acid and a lower alcohol in multi-staged fixed-bed reactors each charged with a weakly acidic solid catalyst and reacting them with each other by feeding the fatty acid to a reactor at an upstream stage and sending it to a stage at the downstream side, feeding the gaseous lower alcohol to a reactor at a downstream stage to carry out downward co-current operation and at the same time returning the gaseous lower alcohol discharged from the outlet of the reactor to a stage at the upstream side to repeatedly conducting a pseudo-countercurrent operation in the fixed bed of each reactor.

5. The process according to claim 1, wherein the weakly acidic solid catalyst has a strong acid point of not higher than 0.2 mmol/g-Cat and a weak acid point of not less than 0.3 mol/g-Cat, each acid point being defined as follows:

Weak acid point: the point at which desorption of $NH_3$ occurs in the range of 100 to 250° C. in TPD (ammonia adsorption-desorption process);

Strong acid point: the point at which desorption of $NH_3$ occurs at a temperature higher than 250° C. in TPD.

6. The process according to claim 1, wherein the weakly acidic solid catalyst is a molded article of a weakly acidic solid catalyst having the structure (A), the structure (B) and the metal atom (C) as follows:

Structure (A): a structure of an inorganic phosphoric acid wherein the hydrogen atom is removed from at least on OH group thereof, Structure (B): a structure of an organic phosphoric acid, represented by the formula (1) or (2), wherein the hydrogen atom is removed from at least on OH group thereof:

-continued

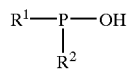

(2)

wherein —$R^1$ and —$R^2$ is independently selected from the group consisting of —R, —OR, —OH and —H and at least one of —$R^1$ and —$R^2$ is —R or —OR, —R being a $C_{1-22}$ organic group, and Metal atom ©: at least one metal atom selected from the group consisting of aluminum, gallium, and iron.

7. The process according to claim 1, wherein the weakly acidic solid catalyst is a molded article of a heterogeneous catalyst comprising aluminum orthophosphate.

* * * * *